United States Patent
Suri et al.

(10) Patent No.: US 8,486,137 B2
(45) Date of Patent: *Jul. 16, 2013

(54) STREAMLINED, APICAL DELIVERY SYSTEM FOR IN SITU DEPLOYMENT OF CARDIAC VALVE PROSTHESES

(75) Inventors: Rakesh M. Suri, Rochester, MN (US); Franco Vallana, Turin (IT); Giovanni Rolando, Chivasso (IT); Giovanni Righini, Chivasso (IT); Brent R. Phillips, Rochester, MN (US); Eric Manasse, Milan (IT)

(73) Assignees: Sorin Group Italia S.r.l., Milan (IT); Mayo Foundation for Medical Education and Research, Rochester, MN (US)

(*) Notice: Subject to any disclaimer, the term of this patent is extended or adjusted under 35 U.S.C. 154(b) by 1212 days.

This patent is subject to a terminal disclaimer.

(21) Appl. No.: 12/147,558

(22) Filed: Jun. 27, 2008

(65) Prior Publication Data

US 2009/0069889 A1 Mar. 12, 2009

Related U.S. Application Data

(63) Continuation of application No. 11/851,528, filed on Sep. 7, 2007, now Pat. No. 8,114,154, which is a continuation of application No. 11/851,523, filed on Sep. 7, 2007.

(51) Int. Cl.
*A61F 2/24* (2006.01)
(52) U.S. Cl.
USPC ............................... 623/2.11; 623/1.11

(58) Field of Classification Search
USPC ................ 623/1.11, 1.12, 1.13, 2.11, 2.14, 623/2.17, 2.18
See application file for complete search history.

(56) References Cited

U.S. PATENT DOCUMENTS

| 3,671,979 A | 6/1972 | Moulopoulos |
| 4,011,947 A | 3/1977 | Sawyer |
| 4,056,854 A | 11/1977 | Boretos et al. |
| 4,477,930 A | 10/1984 | Totten et al. |
| 4,601,706 A | 7/1986 | Aillon |
| 4,624,822 A | 11/1986 | Arru et al. |

(Continued)

FOREIGN PATENT DOCUMENTS

| DE | 19546692 | 6/1997 |
| DE | 19857887 | 7/2000 |

(Continued)

OTHER PUBLICATIONS

European Search Report issued in EP Application No. 08159301, mailed Dec. 30, 2008, 6 pages.

(Continued)

*Primary Examiner* — Gary Jackson
*Assistant Examiner* — Michael Mendoza
(74) *Attorney, Agent, or Firm* — Faegre Baker Daniels LLP

(57) ABSTRACT

A system for implanting a heart valve prosthesis in a patient's heart includes a balloon expandable, tissue, stented heart valve, and an apical valve delivery device for delivering the stented heart valve to a target site in the patient's heart. The delivery device includes an inflation balloon module for expanding the stented heart valve prosthesis, markers on the delivery device to assist in location of the delivery device at an appropriate location, and a streamlined cap.

13 Claims, 14 Drawing Sheets

U.S. PATENT DOCUMENTS

| | | | |
|---|---|---|---|
| 4,684,364 A | 8/1987 | Sawyer et al. | |
| 4,722,725 A | 2/1988 | Sawyer et al. | |
| 4,732,152 A | 3/1988 | Wallsten et al. | |
| 4,758,151 A | 7/1988 | Arru et al. | |
| 4,777,951 A | 10/1988 | Cribier et al. | |
| 4,784,644 A | 11/1988 | Sawyer et al. | |
| 4,994,077 A | 2/1991 | Dobben | |
| 5,057,092 A | 10/1991 | Webster, Jr. | |
| 5,084,151 A | 1/1992 | Vallana et al. | |
| 5,123,919 A | 6/1992 | Sauter et al. | |
| 5,133,845 A | 7/1992 | Vallana et al. | |
| 5,181,911 A | 1/1993 | Shturman | |
| 5,201,757 A | 4/1993 | Heyn et al. | |
| 5,287,848 A | 2/1994 | Cubb et al. | |
| 5,304,189 A | 4/1994 | Goldberg et al. | |
| 5,332,402 A | 7/1994 | Teitelbaum | |
| 5,370,684 A | 12/1994 | Vallana et al. | |
| 5,370,685 A | 12/1994 | Stevens | |
| 5,387,247 A | 2/1995 | Vallana et al. | |
| 5,397,351 A | 3/1995 | Pavcnik et al. | |
| 5,411,552 A | 5/1995 | Andersen et al. | |
| 5,423,886 A | 6/1995 | Arru et al. | |
| 5,445,646 A | 8/1995 | Euteneuer et al. | |
| 5,545,214 A | 8/1996 | Stevens | |
| 5,554,185 A | 9/1996 | Block et al. | |
| 5,556,414 A | 9/1996 | Turi | |
| 5,662,712 A | 9/1997 | Pathak et al. | |
| 5,693,083 A | 12/1997 | Baker et al. | |
| 5,766,151 A | 6/1998 | Valley et al. | |
| 5,772,693 A | 6/1998 | Brownlee | |
| 5,782,811 A | 7/1998 | Samson et al. | |
| 5,824,064 A | 10/1998 | Taheri | |
| 5,840,081 A | 11/1998 | Andersen et al. | |
| 5,849,005 A | 12/1998 | Garrison et al. | |
| 5,855,597 A | 1/1999 | Jayaraman | |
| 5,855,601 A | 1/1999 | Bessler et al. | |
| 5,871,489 A | 2/1999 | Ovil | |
| 5,925,063 A | 7/1999 | Khosravi | |
| 5,951,600 A | 9/1999 | Lemelson | |
| 5,954,766 A | 9/1999 | Zadno-Azizi et al. | |
| 5,957,949 A | 9/1999 | Leonhardt et al. | |
| 5,980,570 A | 11/1999 | Simpson | |
| 6,010,530 A | 1/2000 | Goicoechea | |
| 6,010,531 A * | 1/2000 | Donlon et al. | 623/2.1 |
| 6,029,671 A | 2/2000 | Stevens et al. | |
| 6,030,360 A | 2/2000 | Biggs | |
| 6,090,099 A | 7/2000 | Samson et al. | |
| 6,106,497 A | 8/2000 | Wang | |
| 6,125,852 A | 10/2000 | Stevens et al. | |
| 6,139,572 A | 10/2000 | Campbell et al. | |
| 6,168,614 B1 | 1/2001 | Andersen et al. | |
| 6,251,093 B1 | 6/2001 | Valley et al. | |
| 6,299,638 B1 | 10/2001 | Sauter | |
| 6,309,382 B1 | 10/2001 | Garrison et al. | |
| 6,346,071 B1 | 2/2002 | Mussivand | |
| 6,402,780 B2 | 6/2002 | Williamson, IV et al. | |
| 6,416,474 B1 | 7/2002 | Penner et al. | |
| 6,425,916 B1 | 7/2002 | Garrison et al. | |
| 6,454,799 B1 | 9/2002 | Schreck | |
| 6,458,153 B1 | 10/2002 | Bailey et al. | |
| 6,482,228 B1 | 11/2002 | Norred | |
| 6,572,642 B2 | 6/2003 | Rinaldi et al. | |
| 6,582,462 B1 | 6/2003 | Andersen et al. | |
| 6,607,553 B1 | 8/2003 | Healy et al. | |
| 6,641,558 B1 | 11/2003 | Aboul-Hosn et al. | |
| 6,645,197 B2 | 11/2003 | Garrison et al. | |
| 6,652,578 B2 | 11/2003 | Bailey et al. | |
| 6,685,739 B2 | 2/2004 | DiMatteo et al. | |
| 6,726,648 B2 | 4/2004 | Kaplon et al. | |
| 6,726,712 B1 | 4/2004 | Raeder-Devens et al. | |
| 6,730,118 B2 | 5/2004 | Spenser et al. | |
| 6,733,525 B2 | 5/2004 | Yang et al. | |
| 6,767,362 B2 | 7/2004 | Schreck | |
| 6,769,434 B2 | 8/2004 | Liddicoat et al. | |
| 6,805,711 B2 | 10/2004 | Quijano et al. | |
| 6,830,584 B1 | 12/2004 | Seguin | |
| 6,830,585 B1 | 12/2004 | Artof et al. | |
| 6,875,231 B2 | 4/2005 | Anduiza et al. | |
| 6,893,460 B2 | 5/2005 | Spenser et al. | |
| 6,908,481 B2 | 6/2005 | Cribier | |
| 6,913,618 B2 | 7/2005 | Denardo et al. | |
| 6,945,957 B2 | 9/2005 | Freyman | |
| 6,964,673 B2 | 11/2005 | Tsugita et al. | |
| 6,974,464 B2 | 12/2005 | Quijano et al. | |
| 6,981,942 B2 | 1/2006 | Khaw et al. | |
| 6,991,646 B2 | 1/2006 | Clerc et al. | |
| 7,001,423 B2 | 2/2006 | Euteneuer et al. | |
| 7,018,406 B2 | 3/2006 | Seguin et al. | |
| 7,018,408 B2 | 3/2006 | Bailey et al. | |
| 7,041,132 B2 | 5/2006 | Quijano et al. | |
| 7,044,966 B2 | 5/2006 | Svanidze et al. | |
| 7,077,801 B2 | 7/2006 | Haverich | |
| 7,101,396 B2 | 9/2006 | Artof et al. | |
| 7,144,364 B2 | 12/2006 | Barbut et al. | |
| 7,156,872 B2 | 1/2007 | Strecker | |
| 7,195,641 B2 | 3/2007 | Palmaz et al. | |
| 7,201,761 B2 | 4/2007 | Woolfson et al. | |
| 7,329,279 B2 | 2/2008 | Haug et al. | |
| 7,338,467 B2 | 3/2008 | Lutter | |
| 7,338,520 B2 | 3/2008 | Bailey et al. | |
| 7,374,571 B2 | 5/2008 | Pease et al. | |
| RE40,377 E | 6/2008 | Williamson, IV et al. | |
| 7,399,315 B2 | 7/2008 | Iobbi | |
| 7,544,206 B2 | 6/2009 | Cohn | |
| 7,556,646 B2 | 7/2009 | Yang et al. | |
| 7,618,432 B2 | 11/2009 | Pedersen et al. | |
| 7,708,775 B2 | 5/2010 | Rowe et al. | |
| 7,993,392 B2 | 8/2011 | Rihhini et al. | |
| 8,057,539 B2 | 11/2011 | Ghione et al. | |
| 8,070,799 B2 | 12/2011 | Righini et al. | |
| 2001/0002445 A1 | 5/2001 | Vesely | |
| 2001/0007956 A1 | 7/2001 | Letac et al. | |
| 2001/0010017 A1 | 7/2001 | Letac et al. | |
| 2001/0039450 A1 | 11/2001 | Pavcnik et al. | |
| 2001/0044591 A1 | 11/2001 | Stevens et al. | |
| 2002/0029075 A1 | 3/2002 | Leonhardt | |
| 2002/0042651 A1 | 4/2002 | Liddicoat et al. | |
| 2002/0045846 A1 | 4/2002 | Kaplon et al. | |
| 2002/0058995 A1 | 5/2002 | Stevens | |
| 2002/0099431 A1 | 7/2002 | Armstrong et al. | |
| 2002/0107531 A1 | 8/2002 | Schreck et al. | |
| 2002/0117264 A1 | 8/2002 | Rinaldi et al. | |
| 2002/0123802 A1 | 9/2002 | Snyders | |
| 2002/0138138 A1 | 9/2002 | Yang | |
| 2002/0151970 A1 | 10/2002 | Garrison et al. | |
| 2002/0198594 A1 | 12/2002 | Schreck | |
| 2003/0014104 A1 | 1/2003 | Cribier | |
| 2003/0023300 A1 | 1/2003 | Bailey et al. | |
| 2003/0023303 A1 | 1/2003 | Palmaz et al. | |
| 2003/0033000 A1 | 2/2003 | DiCaprio et al. | |
| 2003/0036795 A1 | 2/2003 | Andersen et al. | |
| 2003/0055495 A1 | 3/2003 | Pease et al. | |
| 2003/0109924 A1 | 6/2003 | Cribier | |
| 2003/0130729 A1 | 7/2003 | Paniagua et al. | |
| 2003/0153974 A1 | 8/2003 | Spenser et al. | |
| 2003/0163194 A1 | 8/2003 | Quijano et al. | |
| 2003/0191521 A1 | 10/2003 | Denardo et al. | |
| 2003/0191528 A1 | 10/2003 | Quijano et al. | |
| 2004/0034411 A1 | 2/2004 | Quijano et al. | |
| 2004/0039371 A1 | 2/2004 | Tockman et al. | |
| 2004/0039436 A1 | 2/2004 | Spenser et al. | |
| 2004/0039442 A1 | 2/2004 | St. Goar et al. | |
| 2004/0049266 A1 | 3/2004 | Anduiza et al. | |
| 2004/0055606 A1 | 3/2004 | Hendricksen et al. | |
| 2004/0078072 A1 | 4/2004 | Tu et al. | |
| 2004/0093060 A1 | 5/2004 | Seguin et al. | |
| 2004/0093063 A1 | 5/2004 | Wright et al. | |
| 2004/0106976 A1 | 6/2004 | Bailey et al. | |
| 2004/0127848 A1 | 7/2004 | Freyman | |
| 2004/0147993 A1 | 7/2004 | Westlund et al. | |
| 2004/0186563 A1 | 9/2004 | Lobbi | |
| 2004/0215333 A1 | 10/2004 | Duran et al. | |
| 2004/0236170 A1 | 11/2004 | Kim | |
| 2004/0249413 A1 | 12/2004 | Allen et al. | |
| 2005/0075584 A1 | 4/2005 | Cali | |
| 2005/0075712 A1 | 4/2005 | Biancucci et al. | |
| 2005/0075713 A1 | 4/2005 | Biancucci et al. | |

| | | |
|---|---|---|
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0075726 A1 | 4/2005 | Svanidze et al. |
| 2005/0075728 A1 | 4/2005 | Nguyen et al. |
| 2005/0075729 A1 | 4/2005 | Nguyen et al. |
| 2005/0075730 A1 | 4/2005 | Myers et al. |
| 2005/0075731 A1 | 4/2005 | Artof et al. |
| 2005/0080476 A1 | 4/2005 | Gunderson et al. |
| 2005/0096993 A1 | 5/2005 | Pradhan et al. |
| 2005/0104957 A1 | 5/2005 | Okamoto et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Salahieh et al. |
| 2005/0137693 A1 | 6/2005 | Haug et al. |
| 2005/0137694 A1 | 6/2005 | Salahieh et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143809 A1 | 6/2005 | Salahieh et al. |
| 2005/0165480 A1 | 7/2005 | Jordan et al. |
| 2005/0197695 A1 | 9/2005 | Stacchino et al. |
| 2005/0240200 A1 | 10/2005 | Bergheim |
| 2005/0251251 A1 | 11/2005 | Cribier |
| 2005/0267493 A1 | 12/2005 | Schreck et al. |
| 2006/0004436 A1 | 1/2006 | Amarant et al. |
| 2006/0004439 A1 | 1/2006 | Spenser et al. |
| 2006/0020333 A1 | 1/2006 | Lashinski et al. |
| 2006/0020334 A1 | 1/2006 | Lashinski et al. |
| 2006/0025844 A1 | 2/2006 | Majercak et al. |
| 2006/0030922 A1 | 2/2006 | Dolan |
| 2006/0063199 A1 | 3/2006 | Elgebaly et al. |
| 2006/0064054 A1 | 3/2006 | Sakakine et al. |
| 2006/0074271 A1 | 4/2006 | Cotter |
| 2006/0074484 A1 | 4/2006 | Huber |
| 2006/0085060 A1 | 4/2006 | Campbell |
| 2006/0095025 A1 | 5/2006 | Levine et al. |
| 2006/0100639 A1 | 5/2006 | Levin et al. |
| 2006/0135962 A1 | 6/2006 | Kick et al. |
| 2006/0142838 A1 | 6/2006 | Molaei et al. |
| 2006/0142848 A1 | 6/2006 | Gabbay |
| 2006/0178740 A1 | 8/2006 | Stacchino et al. |
| 2006/0195134 A1 | 8/2006 | Crittenden |
| 2006/0195184 A1 | 8/2006 | Lane et al. |
| 2006/0229659 A1 | 10/2006 | Gifford et al. |
| 2006/0241656 A1 | 10/2006 | Starksen et al. |
| 2006/0271081 A1 | 11/2006 | Realyvasquez |
| 2006/0276775 A1 | 12/2006 | Rosenberg et al. |
| 2007/0010850 A1 | 1/2007 | Balgobin et al. |
| 2007/0027534 A1 | 2/2007 | Bergheim et al. |
| 2007/0032850 A1 | 2/2007 | Ruiz et al. |
| 2007/0055357 A1 | 3/2007 | Pokorney et al. |
| 2007/0088431 A1 | 4/2007 | Bourang et al. |
| 2007/0100302 A1 | 5/2007 | Dicarlo et al. |
| 2007/0100356 A1 | 5/2007 | Lucatero et al. |
| 2007/0100440 A1 | 5/2007 | Figulla et al. |
| 2007/0112355 A1 | 5/2007 | Salahieh et al. |
| 2007/0112422 A1 | 5/2007 | Dehdashtian |
| 2007/0118207 A1 | 5/2007 | Amplatz et al. |
| 2007/0118209 A1 | 5/2007 | Strecker |
| 2007/0162100 A1 | 7/2007 | Gabbay |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0162113 A1 | 7/2007 | Sharkawy et al. |
| 2007/0173861 A1 | 7/2007 | Strommer et al. |
| 2007/0203503 A1 | 8/2007 | Salahieh et al. |
| 2007/0203561 A1 | 8/2007 | Forster et al. |
| 2007/0203575 A1 | 8/2007 | Forster et al. |
| 2007/0219630 A1 | 9/2007 | Chu |
| 2007/0250097 A1 | 10/2007 | Weitzner et al. |
| 2007/0265702 A1 | 11/2007 | Lattouf |
| 2008/0021546 A1 | 1/2008 | Patz et al. |
| 2008/0065011 A1 | 3/2008 | Marchand et al. |
| 2008/0082165 A1 | 4/2008 | Wilson et al. |
| 2008/0097595 A1 | 4/2008 | Gabbay |
| 2008/0140189 A1 | 6/2008 | Nguyen et al. |
| 2008/0147160 A1 | 6/2008 | Ghione et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0147188 A1 | 6/2008 | Steinberg |
| 2008/0183097 A1 | 7/2008 | Leyde et al. |
| 2008/0208216 A1 | 8/2008 | Cerier |
| 2008/0262507 A1 | 10/2008 | Righini et al. |
| 2009/0069886 A1 | 3/2009 | Suri et al. |
| 2009/0069887 A1 | 3/2009 | Righini et al. |
| 2009/0069890 A1 | 3/2009 | Suri et al. |
| 2009/0105794 A1 | 4/2009 | Ziarno et al. |
| 2009/0118580 A1 | 5/2009 | Sun et al. |
| 2009/0157174 A1 | 6/2009 | Yoganathan et al. |
| 2009/0164004 A1 | 6/2009 | Cohn |
| 2009/0164006 A1 | 6/2009 | Seguin et al. |
| 2009/0171363 A1 | 7/2009 | Chocron |
| 2009/0171456 A1 | 7/2009 | Kveen et al. |
| 2009/0177275 A1 | 7/2009 | Case |
| 2009/0228093 A1 | 9/2009 | Taylor et al. |
| 2009/0234443 A1 | 9/2009 | Ottma et al. |
| 2009/0240326 A1 | 9/2009 | Wilson et al. |
| 2009/0254165 A1 | 10/2009 | Tabor et al. |
| 2009/0281609 A1 | 11/2009 | Benichou et al. |
| 2009/0281619 A1 | 11/2009 | Le et al. |
| 2010/0191326 A1 | 7/2010 | Alkhatib |
| 2010/0292782 A1 | 11/2010 | Giannetti |
| 2010/0292783 A1 | 11/2010 | Giannetti |
| 2010/0292784 A1 | 11/2010 | Giannetti |
| 2012/0053684 A1 | 3/2012 | Righini |

FOREIGN PATENT DOCUMENTS

| | | |
|---|---|---|
| EP | 0133420 | 2/1988 |
| EP | 0155245 B1 | 5/1990 |
| EP | 0592410 | 10/1995 |
| EP | 0512359 | 12/1996 |
| EP | 0515324 B1 | 12/1996 |
| EP | 0850607 | 7/1998 |
| EP | 1057460 | 12/2000 |
| EP | 1088529 | 4/2001 |
| EP | 1356763 A2 | 10/2003 |
| EP | 1356793 | 10/2003 |
| EP | 0852481 B1 | 2/2004 |
| EP | 1440671 A2 | 7/2004 |
| EP | 955895 B1 | 8/2005 |
| EP | 1488735 B1 | 6/2007 |
| EP | 1212989 B1 | 1/2008 |
| EP | 1653884 B1 | 6/2008 |
| EP | 1935377 A1 | 6/2008 |
| EP | 1955643 A1 | 8/2008 |
| EP | 1570809 B1 | 1/2009 |
| EP | 2033581 A1 | 3/2009 |
| EP | 2033597 A1 | 3/2009 |
| FR | 2828091 | 2/2003 |
| WO | 9724989 | 7/1997 |
| WO | 9817202 | 4/1998 |
| WO | 9829057 | 7/1998 |
| WO | WO 99/04728 A1 | 2/1999 |
| WO | 9956665 | 11/1999 |
| WO | WO 00/18303 A1 | 4/2000 |
| WO | 0041652 | 7/2000 |
| WO | WO 00/41652 A1 | 7/2000 |
| WO | WO 01/21244 A1 | 3/2001 |
| WO | 0162189 | 8/2001 |
| WO | 0164137 | 9/2001 |
| WO | 0176510 | 10/2001 |
| WO | 0241789 | 5/2002 |
| WO | 0247575 | 6/2002 |
| WO | 02076348 | 10/2002 |
| WO | 03003943 | 1/2003 |
| WO | 03094797 | 11/2003 |

| | | |
|---|---|---|
| WO | 2004089253 | 10/2004 |
| WO | WO 2005/046525 A1 | 5/2005 |
| WO | WO 2005/065200 A2 | 7/2005 |
| WO | WO 2005/096993 A1 | 10/2005 |
| WO | 2005104957 | 11/2005 |
| WO | 2006054107 | 5/2006 |
| WO | 2006063199 | 6/2006 |
| WO | WO 2006/086135 A2 | 8/2006 |
| WO | 2006116558 | 11/2006 |
| WO | WO 2006/135551 A2 | 12/2006 |
| WO | WO 2006/138173 A2 | 12/2006 |
| WO | WO 2007/071436 A2 | 6/2007 |
| WO | WO 2007/076463 A2 | 7/2007 |
| WO | WO 2008/097589 A1 | 8/2008 |
| WO | WO 2008/125153 A1 | 10/2008 |

OTHER PUBLICATIONS

Partial European Search Report issued in EP Application No. 10155332, dated Jun. 9, 2011, 7 pages.
European Search Report and Search Opinion of European Patent Application No. 06126556.7, dated Jun. 27, 2007.
European Search Report and Search Opinion of European Patent Application No. 07115960.2, dated Jan. 24, 2008.
Huber et al., "Direct-Access Valve Replacement: A Novel Approach for Off-Pump Valve Implantation Using Valved Stents," Journal of the American College of Cardiology, 46(2): 366-370, Jul. 19, 2002.
U.S. Appl. No. 11/851,523, filed Sep. 7, 2007.
U.S. Appl. No. 11/851,528, filed Sep. 7, 2007.
European Search Report Issued in EP Application No. 09160183, dated Oct. 2, 2009, 6 pages.
European Search Report Issued in EP Application No. 09160186, dated Oct. 6, 2009, 5 pages.
European Search Report Issued in EP Application No. 07115951, dated Sep. 24, 2009, 8 pages.
Extended European Search Report issued in EP Application 06126552, dated Jun. 6, 2007, 7 pages.
Extended European Search Report issued in EP Application 09158822, dated Sep. 9, 2009, 5 pages.
Ho, Paul C., "Percutaneous aortic valve replacement: A novel design of the delivery and deployment system", Minimally Invasive Therapy, 2008; 17:3; 190-194.
Partial European Search Report issued in EP App No. 06126556, mailed Apr. 16, 2007, 6 pages.
Extended European Search Report issued in EP Application 06126556, dated Jul. 6, 2007, 13 pages.
Huber et al., "Direct-Access Valve Replacement: A Novel Approach for Off-Pump Valve Implantation Using Valved Stents", Journal for the American College of Cardiology, pp. 366-370, vol. 46, No. 2, Jul. 19, 2005, ISSN: 0735-1097/05, published on-line Jul. 5, 2005.
European Search Report issued in EP Application 08163752, dated Dec. 29, 2008.
European Search Report Issued in EP 09160184 dated Oct. 22, 2009.

* cited by examiner

STREAMLINED, APICAL DELIVERY SYSTEM FOR IN SITU DEPLOYMENT OF CARDIAC VALVE PROSTHESES

CROSS REFERENCE TO RELATED APPLICATION

This application is a continuation of U.S. application Ser. No. 11/851,528, now U.S. Pat. No. 8,114,154, and U.S. application Ser. No. 11/851,523, both filed Sep. 7, 2007, both of which are herein incorporated by reference in their entirety.

PARTIES TO A JOINT RESEARCH AGREEMENT

The invention, as defined by the claims herein, was made by parties to a Joint Research Agreement between Sorin Biomedica Cardio S.r.l. and Mayo Foundation for Medical Education and Research.

TECHNICAL FIELD

The present invention relates to instruments for the in situ delivery and positioning of implantable devices. In particular, the invention relates to the in situ delivery of expandable prosthetic cardiac valves.

BACKGROUND

There is much interest in the medical community in expandable prosthetic valves designed to be implanted using minimally-invasive surgical techniques (e.g., transthoracic microsurgery) or endovascular (i.e., percutaneous) techniques, which are less invasive than the surgical operations required for implanting traditional cardiac-valve prostheses. These expandable prosthetic valves typically include an anchoring structure or armature, which is able to support and fix the valve prosthesis in the implantation position, and prosthetic valve elements (e.g., leaflets or flaps), which are connected to the anchoring structure and are configured to regulate blood flow. One exemplary expandable prosthetic valve is disclosed in U.S. Publication 2006/0178740 A1, which is incorporated herein by reference in its entirety.

Expandable prosthetic valves enable implantation using various minimally-invasive and/or sutureless techniques. Various techniques are generally known for implanting such an aortic valve prosthesis and include percutaneous implantation (e.g., transvascular delivery through a catheter), dissection of the ascending aorta using minimally-invasive thoracic access (e.g., mini-thoracotomy), and transapical delivery in which the aortic valve annulus is accessed directly through an opening in or near the apex of the left ventricle. There is a need in the art for improved systems for delivering the valve prosthesis to an appropriate location in a patient's cardiovascular system.

SUMMARY

The present invention, according to one embodiment, is a cardiac valve implantation system for implanting a cardiac valve prosthesis at an implantation site associated with a cardiac valve annulus. The system includes an expandable cardiac valve prosthesis including a plurality of radially expandable portions and a plurality of valve leaflets. It further includes a deployment instrument including a control handle and a plurality of independently operable deployment elements operable to deploy the plurality of radially expandable portions. The system also includes a delivery device adapted to provide a pathway from outside the patient's body for delivery of the deployment instrument to the implantation site. The delivery device is adapted to provide a de-aired, fluid-filled, or gas-filled environment surrounding the prosthesis.

The present invention, according to another embodiment, is a minimally-invasive method of implanting an expandable cardiac valve prosthesis at an implantation site. The method includes positioning the cardiac valve prosthesis in a deployment instrument including a carrier portion, substantially removing atmospheric air from the carrier portion, advancing the deployment instrument to the implantation site, and deploying the valve prosthesis at the implantation site. The method may include removing air from the carrier portion by filling the chamber with a fluid.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

Figure 1A:
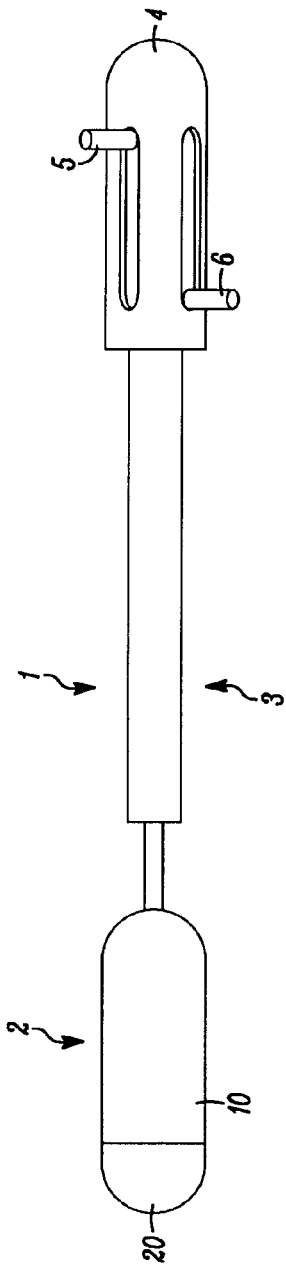
FIGS. 1A and 1B illustrate, in general terms, the delivery instrument of the present invention, according to two exemplary embodiments.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1B:
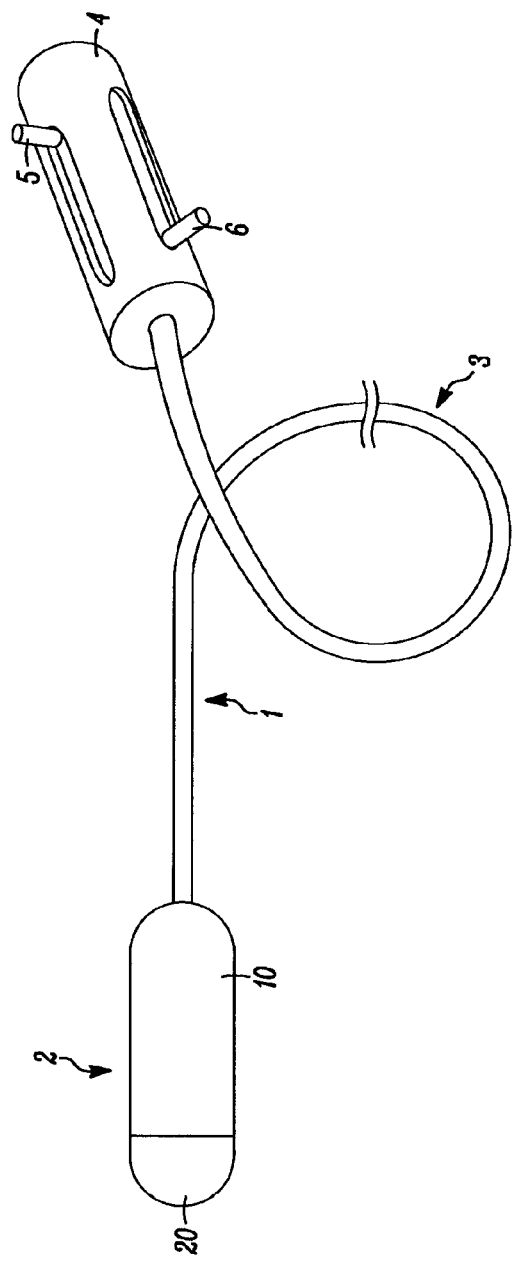

FIGS. 1A and 1B show an instrument 1 for implanting and radially deploying in situ an expandable, prosthetic cardiac valve. Purely by way of example, the prosthetic cardiac valve could be of the type described in U.S. Publication 2006/0178740 A1. As will be apparent to one skilled in the art, however, the instrument 1 could be used to deliver a variety of prosthetic cardiac valves and is not limited to any particular prosthetic valve structure.

As shown in FIG. 1, the instrument 1 includes a chamber or carrier portion 2 for enclosing and carrying the prosthetic device and a manipulation portion 3 that couples the carrier portion 2 to a control handle 4 where two actuator members (for instance two sliders 5, 6) are located. An optional third actuator is provided for that permits the carrier portion 2 to move forward, backward in relation to control handle 4. As will be appreciated, this feature permits for microadjustment of the carrier portion 2 and the valve prosthesis V in relation to a desired location while the control handle 4 is in a fixed location. A further optional actuator on the control handle 4 provides rotational adjustment of carrier portion 2 in relation to manipulation portion 3 and/or control handle 4. This permits the optional placement of the valve prosthesis through at least 360 degrees of rotation.

The manipulation portion 3 may assume various configurations. FIG. 1a shows a configuration where the portion 3 is comprised of a substantially rigid bar with a length (e.g., 10 cm) that will permit positioning of the carrier portion 3, and the prosthetic cardiac valve carried thereby, at an aortic valve site. In various embodiments, instrument 1 is sized and dimensioned to permit easy surgical manipulation of the entire instrument as well as the actuators on the instrument without contacting the patient in a way to interfere with the positioning of the valve prosthesis V.

This configuration is adapted for use, for example, in the sutureless and the transapical implantation methods. FIG. 1B, conversely, shows a second configuration, where the portion 3 is essentially comprised of an elongated, flexible catheter-like member that allows positioning of the carrier portion 3, and the prosthetic cardiac valve carried thereby, at an aortic valve site via transvascular catheterization (e.g., initiating at the femoral artery). This second configuration is also amenable for use in the sutureless or transapical implantation techniques. In one embodiment, the flexible, catheter-like member is braided or otherwise adapted to facilitate transmission of torque from the handle 4 to the carrier portion 2, such that the operator may effect radial positioning of the carrier portion 2 during the implantation procedure. Other features as described for the embodiment in FIG. 1A may also be added to the embodiment in FIG. 1B.

In one embodiment, the instrument 1 is adapted for use with a separate delivery tool. The instrument 1, for example, may be sized and shaped for delivery through a lumen of a tube or trocar during a "sutureless" or transapical delivery technique. Likewise, the instrument 1 may be adapted for delivery through a working lumen of a delivery or guide catheter. In this embodiment, for example, the operator may first deliver a guide catheter through the patient's vasculature to the implant site and then advance the instrument 1 through the lumen. According to another embodiment, the instrument 1 includes an axial lumen extending from a proximal end to a distal end. The lumen is sized to allow introduction and advancement of the instrument 1 over a previously-implanted guide wire. In other embodiments, other techniques known in the art are used to reach the implantation site from a location outside the patient's body.

Figure 2:
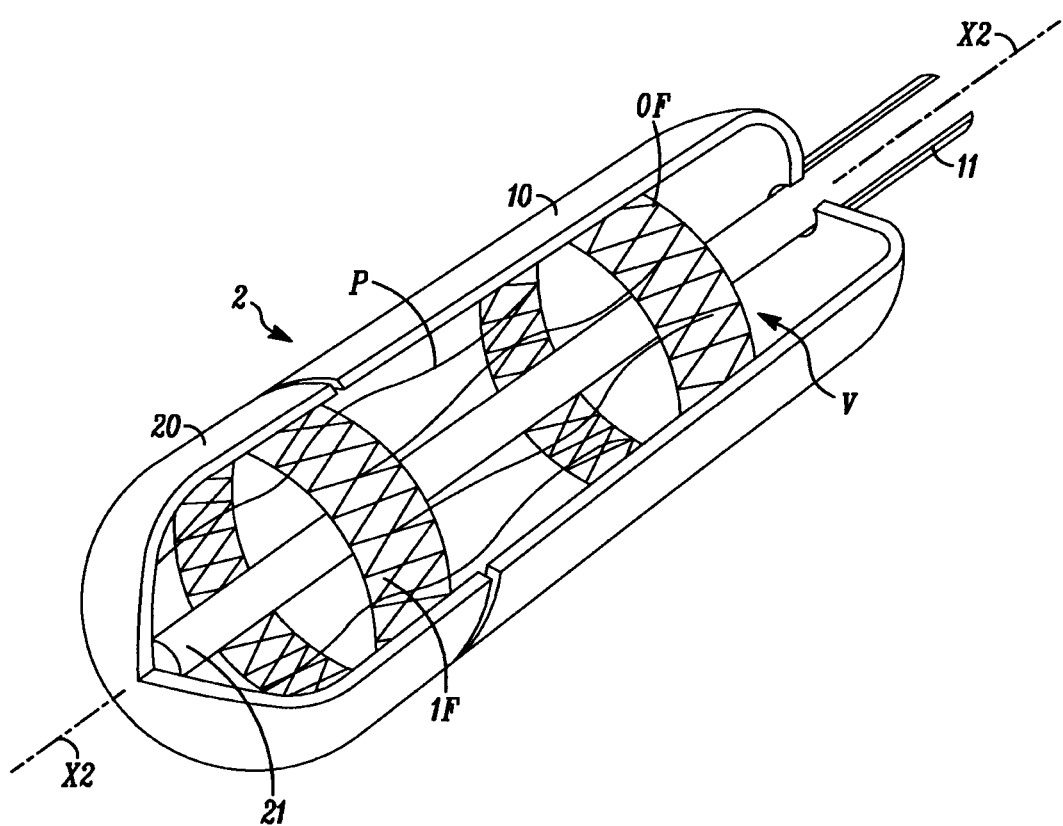
FIG. 2 is a partial cutaway, perspective view of a distal portion of the instrument of FIG. 1, according to one embodiment of the present invention.

As shown in FIG. 2, the carrier portion 2 includes two deployment elements 10, 20, each independently operable to allow the expansion of at least one corresponding, radially expandable portion of the implant device. In the case of the cardiac valve prosthesis, indicated as a whole as V, which is disclosed in U.S. Publication 2006/0178740 A1, two such radially expandable portions are provided situated respectively at the inflow end IF and the outflow end OF for the pulsated blood flow through the prosthesis. In alternative embodiments, however, the cardiac valve prosthesis may include more than two expandable members and, likewise, the carrier portion 2 may include more than two independent deployment elements. The valve prosthesis may be self-expanding (e.g., made from a superelastic material such as Nitinol) or may require expansion by another device (e.g., balloon expansion).

FIG. 2 illustrates an embodiment for use with a self-expanding cardiac valve prosthesis. As shown in FIG. 2, the cardiac valve prosthesis V is arranged within the carrier portion 2, such that an expandable portion IF and an expandable portion OF are each located within one of the deployment elements 10, 20. Each deployment element 10, 20 may be formed as a collar, cap or sheath. In yet a further embodiment, the elements 10, 20 are porous (or have apertures) such that blood flow is facilitated prior, during and after placement of prosthesis V. As will be appreciated, blood flows through the elements 10, 20 and over or through the prosthesis V during the placement procedure. Each deployment element 10, 20 is able to constrain the portions IF, OF in a radially contracted position, against the elastic strength of its constituent material. The portions IF, OF are able to radially expand, as a result of their characteristics of superelasticity, only when released from the deployment element 10, 20. Typically, the release of the portions IF, OF is obtained by causing an axial movement of the deployment elements 10, 20 along the main axis X2 of the carrier portion 2. In one embodiment, the operator (e.g., physician) causes this axial movement by manipulating the sliders 5 and 6, which are coupled to the deployment elements 10, 20.

In yet an alternative embodiment, an optional micro-blood pump is operatively linked to the deployment elements 10 or 20 (or forms a part of the carrier portion 2, and serves to facilitate the movement of blood in a desired direction during the prosthesis placement procedure. The micro-blood pump can have a variable flow rate functionality to regulate blood flow as desired.

In an alternative embodiment (shown in FIGS. 7-9), expansion of the radially expandable portions IF, OF is caused by a positive expansion action exerted by the deployment elements 10, 20. In the embodiments shown in FIGS. 7-9, the deployment elements 10, 20 are comprised of expandable balloons onto which the portions IF, OF are coupled (e.g., "crimped") in a radially contracted position. In this embodiment, the operator causes radial expansion of the portions IF, OF by causing expansion of the balloons, using any of a variety of techniques.

In yet another embodiment of the invention, the delivery instrument 1, including its various portions, is de-aired (i.e., atmospheric air is substantially removed), filled with a fluid (e.g. saline), or filled with an appropriate gas (e.g., carbon dioxide or nitrogen) prior to use. In one embodiment, the lumen of the delivery instrument, which may include a compressed prosthetic valve, is filled with a non-embolytic gas. This process eliminates the risk of an embolism occurring through the introduction of any of the portions described above directly into the beating heart of the patient. According to one exemplary embodiment of the present invention, the delivery instrument, in particular the manipulator portion 3, may include an injection port adapted to mate with a syringe adapted for delivering a fluid or a gas to the delivery instrument. The injection port may include a seal for maintaining fluid pressure in the lumen and may include on or more pressure regulation devices.

According to another exemplary embodiment, a vacuum may be applied to the delivery instrument via a manifold at the proximal end of the manipulator portion 3. The applied vacuum ensures that all oxygen has been evacuated from the delivery tool. Additionally, the carrier portion 2 and the prosthetic valve therein may be assembled and sealed under vacuum.

According to yet another exemplary embodiment, the delivery instrument may be assembled in an environment saturated with a fluid, such as saline, or a gas, such as $CO_2$. For example, the carrier portion 2 and the prosthetic valve therein may be assembled in a saline or $CO_2$ saturated environment such that the carrier portion 2 is filled with the fluid, while the prosthetic valve is loaded into the chamber or carrier portion of the delivery instrument. According to various embodiments, the fluid includes a drug (e.g., heparin) selected to assist with the delivery of the prosthesis. The drug may, for example, include any drug known to manipulate or enhance cardiac function. According to other embodiments, the fluid includes an electrolytic solution.

FIGS. 3-5 illustrate exemplary deployment techniques for the embodiment wherein the expandable portions IF, OF are made of a self-expandable material. In FIGS. 3-5, only the armature of the prosthetic cardiac valve prosthesis V is schematically shown (i.e., the valve leaflets are not shown). As shown, the armature includes the expandable entry (inflow) portion IF and the expandable exit (outflow) portion OF, which are connected axially by anchoring formations P. In one embodiment, as described in U.S. Publication 2006/0178740, the formations P are spaced at 120° intervals about the armature circumference and are configured to radially protrude from the prosthesis V so as to penetrate into the sinuses of Valsalva.

In the case of a cardiac valve prosthesis to be deployed at an aortic position, the inflow end IF of the prosthesis V is located in correspondence with the aortic annulus, thereby facing the left ventricle. The profile of the aortic annulus is shown schematically by the dashed lines A in FIGS. 3-5. Conversely, the outflow end OF is located in the ascending line of the aorta, in a position immediately distal to the sinuses of Valsalva, wherein the formations P extend. The elements 10, 20 are in a further embodiment sized and dimensioned to accommodate anchoring elements of prosthetic valve V. This dimensioning can take the form in one embodiment of appropriate tailored protuberances that permit the anchoring elements to rest in an appropriately contracted position prior to positioning.

FIGS. 3-5 show a carrier portion 2 having two deployment elements 10, 20 each of which is capable of "encapsulating" (on one embodiment) or restraining a respective one of the inflow IF and outflow OF portions, to constrain the portions IF, OF from radially expanding. Both the elements 10, 20 can be arranged to slide longitudinally with respect to the principal axis X2 of the carrier portion 2. In yet another variant, the elements 10, 20 slide down and rotate around the principal axis X2 (e.g. in a cork screw fashion). The axial (and optional rotational) movement of the elements 10, 20 is obtained, according to exemplary embodiments, via the sliders 5, 6 provided on the handle 4 at the proximal end of the manipulation portion 3 of the instrument 1. For instance, the slider 5 may act on the deployment element 20 through a respective control wire or tendon 21, while the slider 6 may act on the deployment element 10 through a tubular control sheath 11 slidably arranged over the tendon 21, with both the sheath 11 and tendon 21 slidable along the axis X2.

In one exemplary embodiment, an internal surface of the elements 10, 20 comprise a low-friction or lubricious material, such as an ultra-high molecular weight material or PTFE (e.g., Teflon®). Such a coating will enable the elements 11, 21 to move or slide with respect to the portions IF, OF, such that the portions IF, OF are released upon axial movement of the elements 11, 21. In yet a further embodiment, other surfaces of the elements 10, 20 or any other parts of device 1 are coated or made from a low-friction material to provide for ease of insertion and manipulation within a subject.

In one embodiment, the sheath 11 is movable in a distal-to-proximal direction, so that the sheath and thus the element 10 move or slide "backwards" with respect to the carrier portion 2. In a complementary manner, the sliding movement of the tendon 21 will take place in a proximal-to-distal direction, so that the tendon and thus the element 20 move or slide "forward" with respect to the carrier portion 2. In another embodiment, movement of the elements 10, 20 is obtained by manipulating rigid actuation members from the handle 4.

In yet a further embodiment, while the device 1 is shown as being manually operable by a user, it is within the spirit of the invention, to have device 1 and the various positioning elements actuated by sensors (positional) and movement of the various elements of the device control by servo-motors, a microprocessor, and the like (e.g., computer controlled). It is appreciated that placement of the prosthesis V may be more precisely controlled through computer control and mechanical movement of the various elements of device.

Figure 4A:
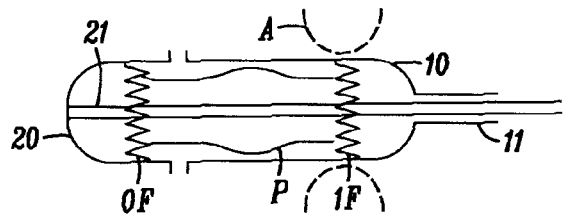
FIGS. 4A-4E illustrate a sequence of deploying a prosthetic heart valve using an antegrade approach, according to another embodiment of the present invention.
Figure 4B:
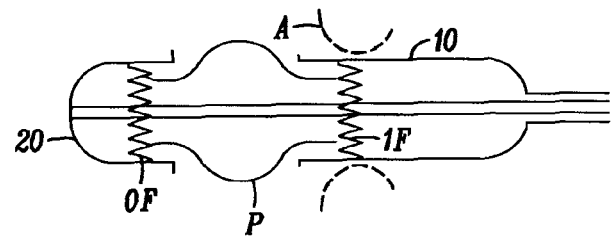
Figure 5A:
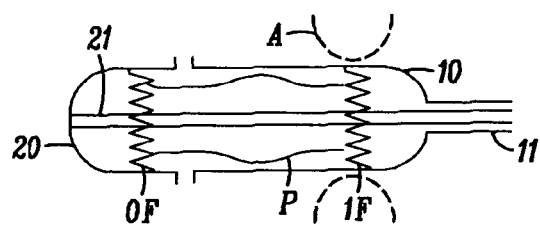
FIGS. 5A-5C illustrate a sequence of deploying a prosthetic heart valve, according to yet another embodiment of the present invention.
Figure 5B:
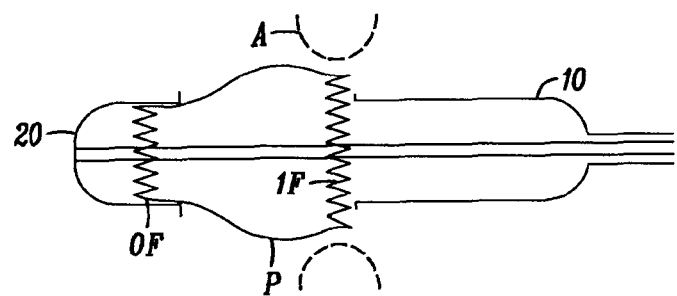
Figure 5C:
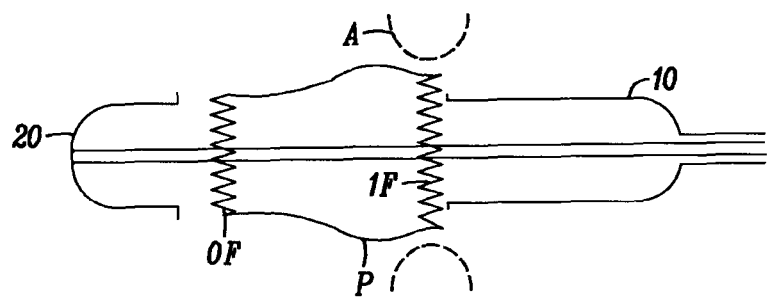
Figure 6:
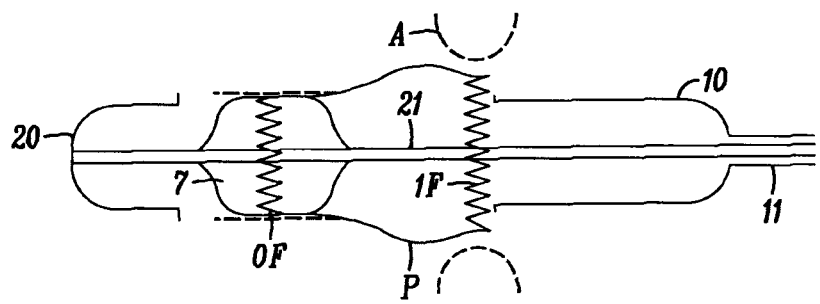
FIGS. 6-9 illustrate further possible features of the instrument illustrated herein, according to various embodiments of the present invention.

FIGS. 3-5 are deliberately simplified for clarity of representation and do not take into account, for instance, the fact that the portion 3 of the instrument may include other control tendons/sheaths and/or ducts for inflating the post-expansion balloons (see FIG. 6). Also, the element 20 could be actuated by means of a sheath rather than a tendon. Also, whatever their specific form of embodiment, the actuator members 11, 21 of the deployment elements 10, 20 may also have associated locking means (not shown, but of a known type) to prevent undesired actuation of the deployment elements 10, 20.

Notably, the deployment elements 10, 20 are actuatable entirely independently of each other. This gives the operator complete freedom in selecting which of the portions IF, OF to deploy first according to the specific implantation method or conditions. FIGS. 3A-3E, for example, illustrate use of the instrument 1 for a "retrograde" approach (e.g., in the case of sutureless or percutaneous implantation), to the valve annulus, wherein the cardiac valve prosthesis V approaches the valve annulus from the aortic arch.

Figure 3A:
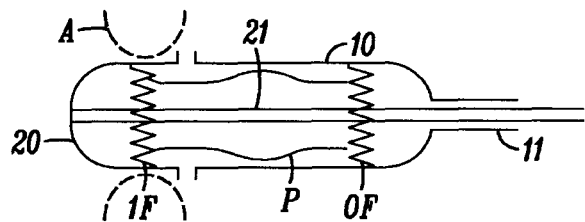
FIGS. 3A-3E illustrate a sequence of deploying a prosthetic heart valve using a retrograde approach, according to one embodiment of the present invention.

In FIG. 3A (as in the following FIGS. 4A and 5A), the cardiac valve prosthesis V is shown mounted in or carried by the carrier portion 2 of the instrument 1, such that the deployment elements 10, 20 constrain the annular ends IF, OF of the prosthesis V in a radially contracted position.

Figure 3B:
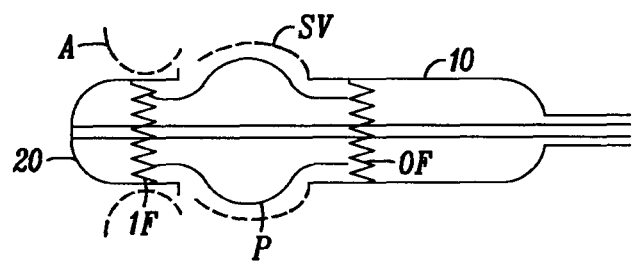

FIG. 3B shows the element 10 retracted axially with respect to the axis X2 of the carrier portion 2 a sufficient distance to uncover and release the formations P, which are then able to expand (e.g., due to their superelastic construction) such that they protrude beyond the diameter of the elements 10, 20. As shown in FIG. 3B, the formations P are allowed to expand, while the remaining portions of the prosthesis V are maintained in a radially contracted configuration. In the configuration shown in FIG. 3B, the operator can take the necessary action for ensuring the appropriate positioning of the prosthesis V in correspondence with the sinuses of Valsalva SV. The profile of the sinuses of Valsalva are shown schematically in FIG. 3B by the dashed lines SV. Prosthesis V has elements sized and dimensioned to completely conform to the sinuses Valsalva in one variant of the invention.

Such appropriate positioning includes both axial positioning (i.e. avoiding deploying the prosthetic valve V too far "upstream" or too far "downstream" of the desired position with the ensuing negative effect that the inflow end IF is not correctly positioned with respect to the valve annulus A) and radial positioning. The sinuses of Valsalva are configured as a hollow, three-lobed structure. Accordingly, accurately positioning each formation P of the prosthesis V in a respective sinus of Valsalva will ensure the correct positioning or angular orientation of the prosthetic valve as a whole, which will ensure that the leaflets of the prosthetic valve are correctly oriented (i.e., extend at the angular positions of the annulus where the natural valve leaflets were located before removal).

In exemplary embodiments, the instrument 1 may further include various structures or features to assist the operator in obtaining the appropriate axial positioning with respect to the aortic annulus and radial positioning with respect to the sinuses of Valsalva. The instrument 1 (or the guide catheter or delivery tube), for example may include a lumen sufficient to allow the injection of contrast fluid to a location at the implantation site. For the embodiment shown in FIG. 3, for example, this lumen would have an opening located past the inflow end IF or the prosthesis V, such that any injected contrast fluid would then flow back toward the prosthesis V, thereby enabling the operator to obtain a visual image of the implantation site, including an image of the sinuses of Valsalva. Likewise, in other embodiments, the prosthesis V may include radiopaque markers disposed at appropriate locations to assist in this positioning.

In one exemplary embodiment (e.g., in the case of "sutureless" implantation), the carrier portion 2 and the prosthesis V may be arranged from the beginning in the configuration represented in FIG. 3B, namely with the formations P already protruding radially with respect to the profile of the prosthesis, while the annular end portions IF, OF are constrained in a radially contracted position by the elements 10, 20. In this case, the element 10 will have a sufficient length only to cover the axial extension of the annular end portion OF, as it need not radially constrain the formations P.

Figure 3C:
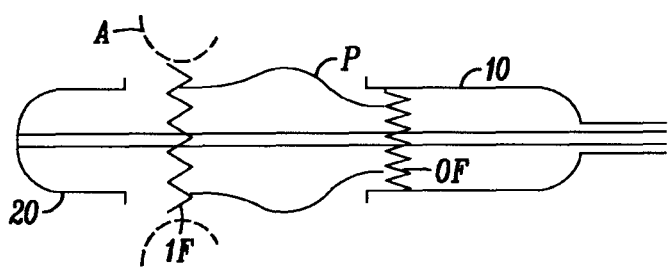
Figure 3D:
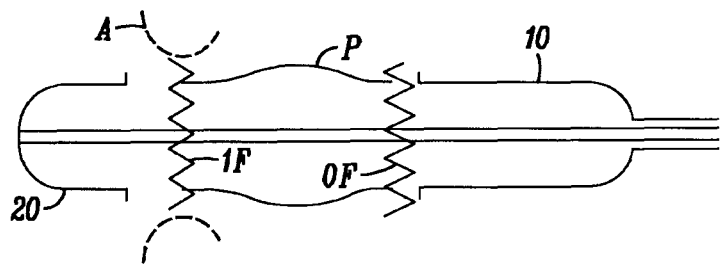

FIG. 3C shows the element 20 displaced distally with respect to the prosthesis V by the tendon 21. As shown, the element 20 was displaced a length sufficient to uncover the annular inflow portion IF, such that the portion IF is able to expand radially to assume the desired anchoring position at the valve annulus A. This release of the inflow portion IF takes place while the prosthetic valve V is still precisely retained and controlled by the instrument 1, such that it will not move or "jump" with respect to the valve annulus during the expansion of the portion IF.

It will also be appreciated that from the configuration shown in FIG. 3C, the operator may return to the configuration shown in FIG. 3A, so as to cause a radial contraction of the formations P and, even if in an incomplete manner, of the annular inflow portion IF. This will allow the operator to withdraw the prosthesis V from the implantation site if the operator believes that the implantation procedure has thus far not yielded a satisfactory result. In this variant, a re-contracting element is provided as part of device 1 that permits either the outflow OF and/or inflow IF portion to be re-constricted. By way of example a cutable thread could be used to re-crimp either portion.

Next, the prosthetic implantation process progresses by sliding the deployment element 10 so that it releases the outflow annular portion OF. The portion OF can then radially expand against the aortic wall, thus completing the second phase of the implantation operation of the prosthesis V.

Figure 3E:
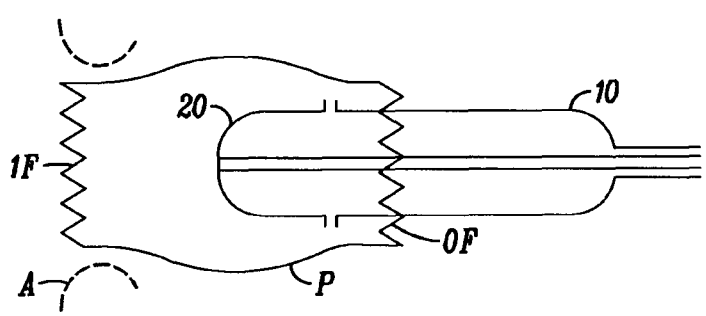

Finally, as shown in FIG. 3E, the carrier portion 2 and the instrument 1 as a whole can be withdrawn with respect to the implantation site through the center of the prosthesis V. In one embodiment, the carrier portion 2 is withdrawn after the deployment elements 10, 20 have been brought back to their initial positions, that is after having caused the elements 10, 20 to slide, in a proximal-to-distal and in a distal-to-proximal direction, respectively. The sequence of operations represented in FIGS. 3A-3E may be accomplished with a pulsating heart and without interrupting the natural circulation of blood.

According to another exemplary embodiment, the instrument 1 can be adapted such that substantially oxygen-free environment can be maintained through out the valve implantation procedure. According to one embodiment, the instrument can include a seal or one or more pressure sensors and/or regulators for maintaining a constant flow a fluid, such as saline, or a constant pressure of $CO_2$ at the implantation site through the delivery instrument 1 in order to minimize and/or prevent air embolism during the procedure.

FIGS. 4A-4E show an implantation procedure of a prosthesis V, according to another embodiment of the present invention. This procedure is similar to the procedure shown in FIGS. 3A-3E, but FIGS. 4A-4E show an "antegrade" approach, typical of a transapical implantation procedure. In this case, the prosthesis V (mounted in the carrier portion 2) is advanced to the implantation site (e.g., aortic valve) through the left ventricle. While reference is again made herein to a prosthetic valve for the substitution of the aortic valve, it will be once more appreciated that the same criteria and principles will also apply to different valve types (e.g. mitral). Various techniques for accessing the aortic valve site through the left ventricle are known in the art. One exemplary technique for transapical delivery is disclosed in U.S. Publication 2005/0240200, which is incorporated by reference herein.

FIGS. 4A-4E are substantially identical to FIGS. 3A-3E, except that the position assumed by the prosthetic valve V is inverted. Accordingly, in the case of the intervention of "antegrade" type of FIGS. 4A-4E, the carrier portion 2 of the instrument 1 with the prosthesis V mounted therein is passed completely through the valve annulus A, so as to position the inflow portion IF in correspondence with the valve annulus A. As it is appreciated the device 1 is configured and sized and dimensioned so that it is capable of delivering the prosthesis V in both an antegrade and a retrograde intervention.

Figure 4C:
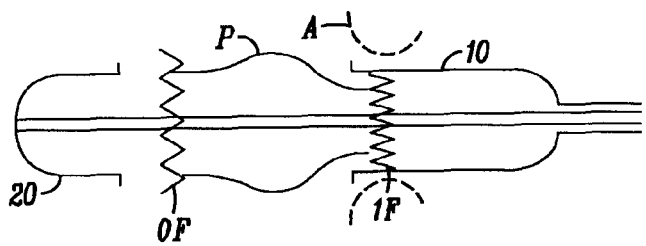

After withdrawing the deployment element 10, so as to release the formations P (FIG. 4B), the deployment element 20 is advanced distally, so as to release and allow the outflow annular end portion OF to radially expand against the aortic wall downstream of the sinuses of Valsalva (see FIG. 4C). At this point, the operator is still in a position to ensure that the prosthesis has the required correct angular position by making sure that the formations P each correctly engage a corresponding sinus. If the formations P do not properly align with the sinuses of Valsalva, the operator may use the instrument to apply a torque to the prosthesis V, thereby causing a rotation of the prosthesis V into the proper angular position. In one exemplary embodiment, the tendon 21 includes a stop (not shown) configured to prohibit axial motion of the inflow portion IF. This stop may help prevent axial movement of the inflow portion IF during distal motion of the of the deployment element 20, thereby ensuring that the outflow portion OF is released before the inflow portion IF.

Figure 4D:
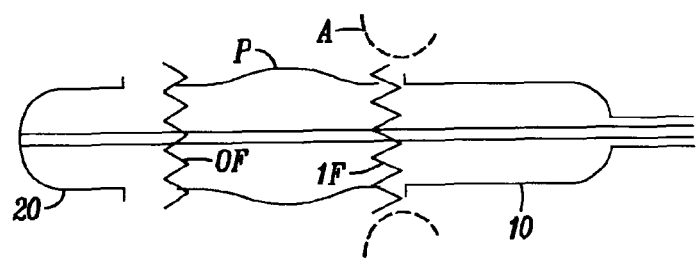
Figure 4E:
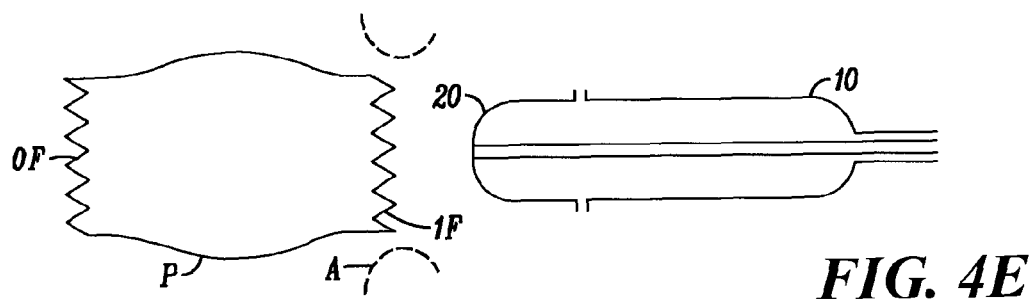

Subsequently, by completely withdrawing in a proximal direction the deployment element 10, the operator releases the annular inflow portion IF that is thus deployed in correspondence with the aortic valve annulus thus completing the two-step implantation procedure of the prosthetic valve V (see FIG. 4D). Then, according to one embodiment, the procedure progresses by bringing the deployment elements 10, 20 back towards their initial position with the ensuing retraction of the instrument 1 from the inflow portion IF of the valve (FIG. 4E).

FIGS. 5A-5C, which correspond closely to the sequence of FIGS. 4A-4C, show that (also for a procedure of the "antegrade" type) it is possible to effect the two-step implantation sequence of FIGS. 4A-4E by deploying the end portions IF and OF of the prosthetic valve V in the reverse order. In the technique of FIGS. 5A-5C, once the desired "axial" position is reached (as represented in FIG. 5A, which is practically identical to FIG. 4A) with the expandable inflow end IF in correspondence of the aortic valve annulus A, the inflow portion IF is expanded first by operating the deployment element 10 to release the corresponding inflow portion IF.

The implantation procedure then proceeds, as schematically represented in FIG. 5C, with the second step of this two-step procedure, namely with the deployment element 20 advanced distally with respect to the prosthesis V so as to release the expandable outflow portion OF. The outflow portion OF is thus free to expand against the aortic wall in a region downstream of the sinuses of Valsalva into which the formations P protrude.

The teaching provided in FIGS. 5A-5C also apply in the case of a "retrograde" procedure, as shown in FIGS. 3A-3E. Because the deployment elements 10, 20 are adapted to be activated entirely independently of each other, the operator is free to choose the most suitable deployment sequence (inflow first and then outflow; outflow first and then inflow) as a function of the specific conditions of intervention. This sequence may be entirely independent of access to the implantation site being of the retrograde or antegrade type.

Figure 7:
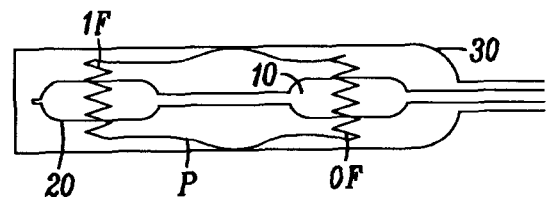

FIGS. 6 and 7 schematically illustrate embodiments in which the carrier portion 2 of the instrument 1 includes a balloon 7 at locations corresponding to at least one or to both annular ends of the cardiac valve prosthesis V. This balloon may be of any known type (e.g. of the type currently used in expanding stents or the like in a body lumen, which therefore does require a detailed description to be provided herein) and is intended for use in realizing a "post-expansion" of the corresponding end portion IF, OF of the prosthesis V, so as to radially urge it against the wall of the implantation lumen. For instance, as shown in FIG. 6, the balloon 7 can be selectively expanded (by inflating it with well known means and criteria) in such a way as to produce a radial expansion of the expandable portion associated therewith (here the end portion OF).

This technique may be useful to avoid movement or "jumping" of the prosthesis V during implantation. For instance, if the operator fears that deployment of the inflow end portion IF in correspondence of the aortic annulus A may give rise to an undesired longitudinal displacement of the valve prosthesis V as a whole, while the inflow portion IF is being released by the element 10 and expands to engage the aortic annulus A, a post-expansion balloon 7 associated with the outflow end OF can be inflated. In this way, as long as the post-expansion balloon 7 is kept dilated, the outflow end OF is urged and thus safely anchored to the lumen wall and any undesired displacement of the prosthetic valve V in an axial direction is prevented. Once the inflow portion IF is safely positioned at the aortic annulus A, the balloon 7 can be deflated and the instrument 1 withdrawn.

Figure 8:
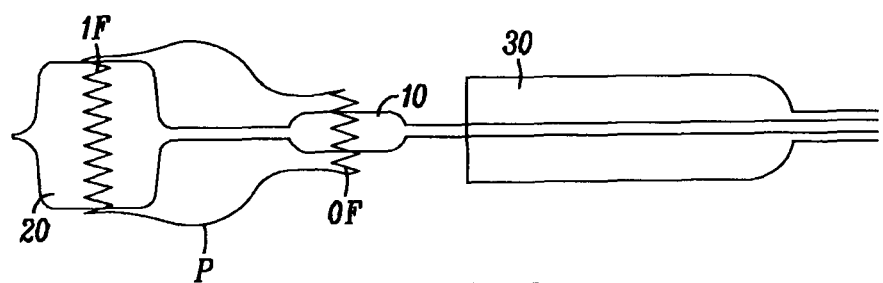
Figure 9:
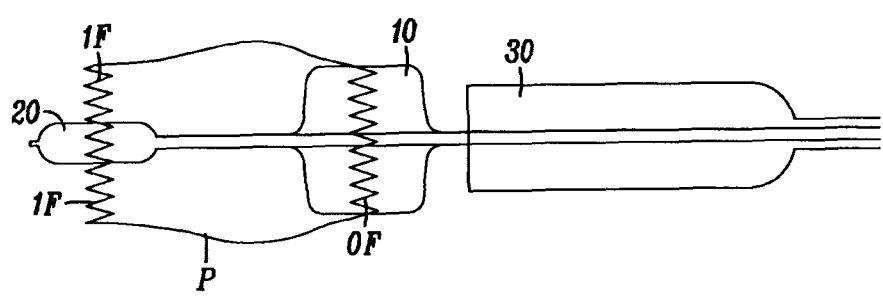
Figure 10A:
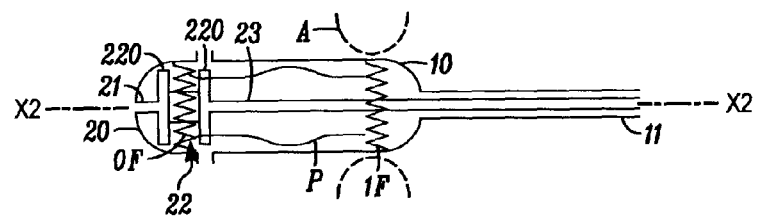
FIG. 10A-10D illustrate a sequence of deploying a prosthetic heart valve, according to another embodiment of the present invention.
Figure 10B:
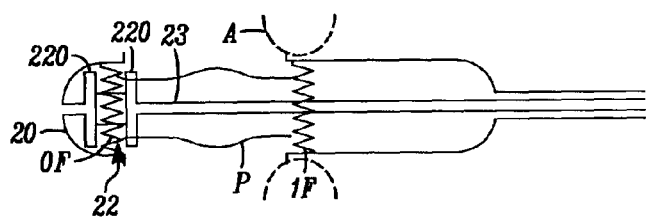
Figure 10C:
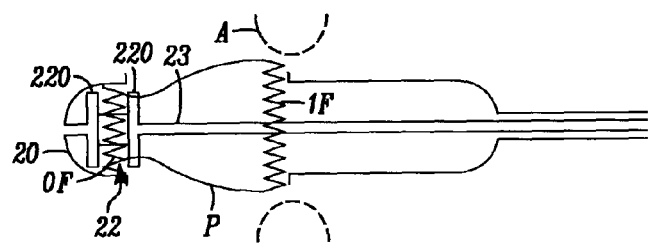
Figure 10D:
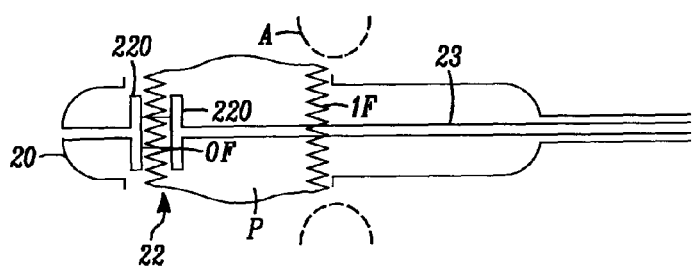

FIGS. 7, 8 and 9 schematically illustrate, without the intent of making any specific distinctions between "antegrade" and "retrograde" approaches and any specific choice as to which end portion, inflow IF or outflow OF, is to be deployed first, that the same two-step mechanism for independently deploying the two end portions IF, OF illustrated in FIGS. 3, 4 and 5 can be implemented in the case of prostheses V including end portions IF, OF whose radial expansion is obtained via a positive outward expansion action exerted by means of deployment elements 10, 20 altogether constituted by expandable balloons. These may be balloons of any known type and substantially correspond, from a structural point of view, to the post-expansion balloons (see for instance the balloon 7 of FIG. 6).

Other embodiments of the present invention include "hybrid" solutions, where a cardiac valve prosthesis V includes one or more self-expandable portions (having associated deployment elements 10, 20 of the type illustrated in FIGS. 2-5) as well as one or more portions radially expandable via an expandable deployment element (such as a balloon as illustrated in FIGS. 7-9).

In one variant and in the case where expansion due to a positive action of one or more balloons is preferred over the use of a self-expandable portion, the same balloon may be used both as an expansion balloon (FIGS. 7, 8 and 9), and as a post-expansion balloon (FIG. 6).

As schematically illustrated in FIGS. 7-9 (the same solution can be adopted also in the case of FIGS. 2-6, it is possible to provide a tubular sheath 30 that surrounds in the manner of a protective tunic the assembly comprised of the carrier portion 2 with the prosthetic valve V mounted therein. This with the purpose of facilitating, typically in a percutaneous implantation procedure, the advancement towards the implantation site through the tortuous paths of the vasculature of the patient without risks of undesired jamming or kinking. It will be appreciated that, for the same goal, the deployment elements 10, 20 normally exhibit a "streamlined" shape, exempt from protruding parts and/or sharp edges. This is particularly the case for the element 20 located at a distal position, which typically exhibits an ogive-like shape.

In yet another variant of the invention, the elements 10, 20 are formed of a material that permits them to collapse after deployment of the prosthesis V. It is appreciated that this permits the entire device to be more easily removed from the subject.

FIGS. 10A-10D, which substantially correspond to FIGS. 5A-5C, illustrate an embodiment associating with either or both of the annular end portions IF, OF of the prosthesis V and "anti-skid" locking member 22. This member is primarily intended to prevent any undesired sliding movement of the end portion (IF and/or OF) with respect to its deployment element lengthwise of the carrier portion 2. Such a locking member is preferably associated with (at least) the annular end portion to be deployed second in the two-step deployment process of the prosthetic valve V described herein.

In this exemplary embodiment, the locking member 22 takes the form of a hub positioned at the distal end of a tubular member 23 having the wire 21 slidably arranged therein. The sheath 11 surrounds the tubular member 23 and is adapted to slide thereon so that the locking member 22 is capable of maintaining at a fixed axial position (e.g. via end flanges 220) the annular outflow portion OF with which the locking member is associated. The annular end portion in question is thus prevented from sliding axially of the deployment element 20, at least as long as the annular end portion OF is radially constrained by the deployment element 20.

The arrangement described makes it possible to adjust the position of the annular end portion locked by the locking member (and the position of the valve prosthesis V as a whole) both axially and angularly to the implantation site. This applies more or less until the annular portion expands to the point where further displacement is prevented by engagement of the annular portion with the valve annulus or the aortic wall. Additionally, the presence of the locking member(s) 22 facilitates possible recovery of the prosthetic valve V in case the implantation procedure is to be aborted.

According to various embodiments of the present invention, the delivery system is capable of both antegrade and retrograde delivery of instruments and the like. One exemplary embodiment of such a delivery system is disclosed in co-pending, commonly assigned U.S. patent application Ser. No. 11/851,523, filed on Sep. 7, 2007, entitled "Prosthetic Valve Delivery System Including Retrograde/Antegrade Approach," which is hereby incorporated by reference in its entirety.

Figure 11:
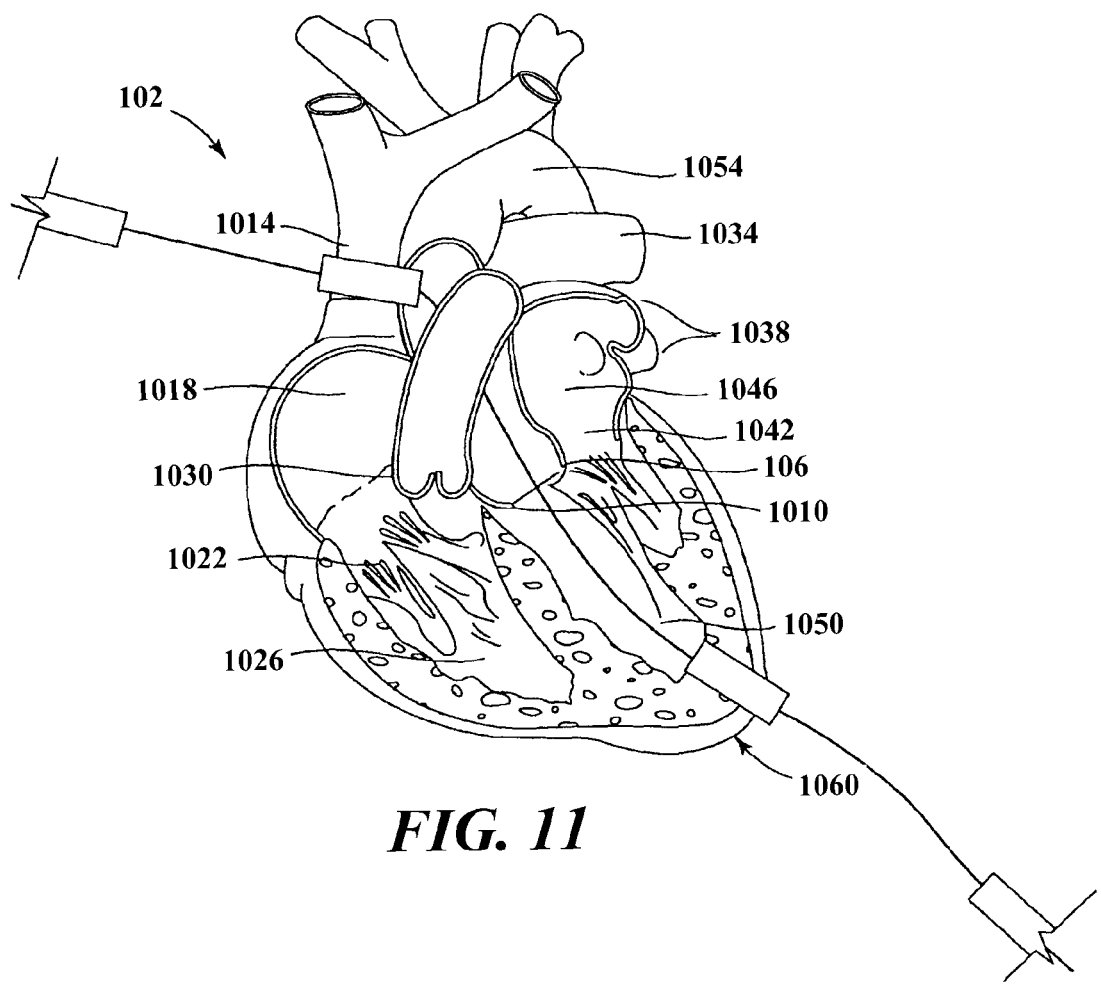
FIG. 11 is a cross-sectional view of a human heart including a prosthetic heart valve.

FIG. 11 is a cross-sectional view of a human heart 102 with an expandable prosthetic heart valve 106 implanted within or adjacent an aortic valve annulus 1010. Blood flows from the superior and inferior vena cavas 1014 into a right atrium 1018 of the heart 102 and then flows through a tricuspid valve 1022 into a right ventricle 1026. A pulmonary valve 1030 facilitates blood flow from the right ventricle 1026 to the pulmonary arteries 1034. The blood is then oxygenated by the lungs and returned back to the heart via pulmonary veins 1038. A mitral valve 1042 then facilitates blood flow from a left atrium 1046 to a left ventricle 1050. Blood then flows from the left ventricle 1050, through the aortic valve annulus 1010, to the aorta 1054. The aorta 1054 then delivers the blood to the coronary arteries and the peripheral vascular system.

Using techniques well known to those of skill in the art, access to the heart 102, according to some embodiments, is established percutaneously through the aorta, femoral, radial or brachial arteries using a retrograde approach to reach a target site within the heart 106 (e.g. the aorta 1054 or aortic valve annulus 1010). Likewise, according to some embodiments, access to the aortic valve annulus is accomplished using a retrograde, minimally-invasive surgical technique to provide access to the aortic valve annulus 1010 through an opening in the aortic arch.

Alternatively, according to various embodiments, access to the heart 102 and the aortic valve annulus 1010 is established through the apical area 1060 (e.g., apex) of the heart. In these embodiments, a percutaneous access port may be established through a patient's chest wall and into the left ventricle at or near the apex 1060. According to some embodiments, access to the left ventricle 1050 through the apex 1060 is established using one of the methods and devices generally shown and described in U.S. Pat. No. 6,010,531, entitled "Less-invasive Devices and Methods for Cardiac Valve Surgery", which is incorporated herein by reference.

The apex 1060 of the heart 102 is generally the blunt rounded inferior extremity of the heart 102 formed by the left and right ventricles, 1026 and 1050. In normal healthy humans, the apex 1060 generally lies behind the fifth left intercostal space from the mid-sternal line. Access to the valve annulus 1010 through the apex 1060 can be established using a larger diameter access port than is possible using percutaneous access methods. Thus, apical access to the heart 102 permits greater flexibility with respect to the types of devices and surgical methods that may be performed in the heart and great vessels.

FIGS. 12-16 show schematic views of exemplary embodiments of a valve access system 1070 for delivering a replacement heart valve to a target site in a patient's heart 102. The valve access system 1070 of the present invention allows for an antegrade as well as a retrograde approach to a target site within the heart 102. Exemplary target sites include native heart valves (e.g. pulmonary, mitral, aortic, and tricuspid) needing repair and/or replacement. While FIGS. 12-16 show the valve access system 1070 traveling through the aortic arch, in alternative embodiments, the system 1070 could exit the vasculature through the aorta and patient's body through a slit or opening in the wall of the aortic vessel.

Figure 12:
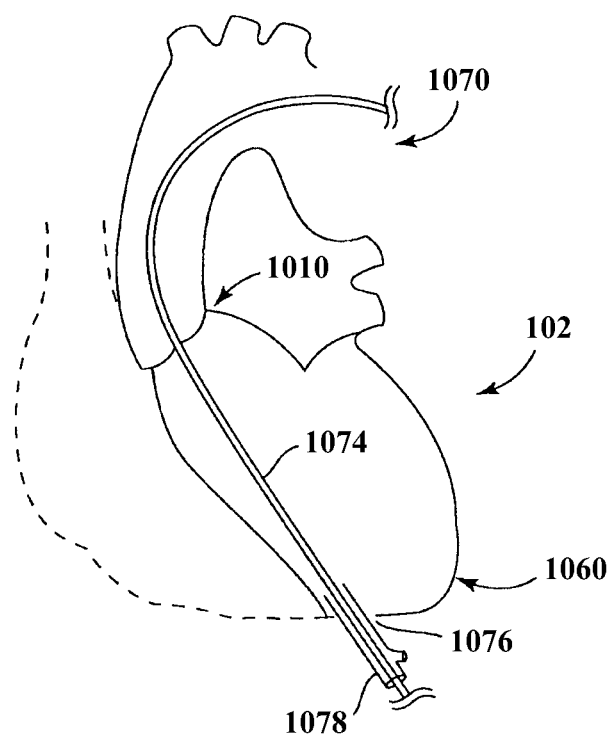
FIG. 12 is a schematic view of the left side of the heart including an implantation device according to an embodiment of the present invention.

According to the embodiment of FIG. 12, the valve access system 1070 includes an implantation device 1074 and is configured to deliver a prosthetic heart valve to a target site within a patient's heart 102. The implantation device 1074 is configured to serve as a rail or track for providing access to the target site from a location outside the patient's body. According to one embodiment of the present invention, the implantation device 1074 is a thin, flexible guidewire or a somewhat thicker wire, such as a stylet. According to an alternative embodiment of the present invention, the implantation device is a guide catheter. The guide catheter is adapted to provide passage to a variety of devices compatible with the valve access system of the present invention. According to one embodiment, the implantation device is reversibly lockable.

The implantation device 1074 is of sufficient size and length to pass through a first opening in a patient's body (e.g., an aorta or a femoral artery access point), through a patient's aorta 1054, and to exit through an access port 1076 established in a patient's left ventricle 1050 at or near the apex 1060. The implantation device 1074 then extends through a transthoracic port 1078, which provides access through the patient's thoracoabdominal (e.g., intercostal) region and into the left ventricle 1050 at or near the apex 1060. The transthoracic port according to various exemplary embodiments is one of an introducer, trocar, or cannula, as is generally known in the art. According to one exemplary embodiment of the present invention, the port 1078 includes one or more hemostasis valves or seals. The hemostasis valve or seal is adapted to provide a blood tight seal against any blood loss or leakage during the procedure, and can be used at the apex, at the aorta, or in both locations. The port 1078 is configured to allow passage of the implantation device, catheter, or any tools or devices to be delivered to the target site using the implantation device, while at the same time providing a blood tight seal against blood loss or leakage.

According to one exemplary technique for introducing the access system 1070, a physician establishes an access port into the patient's aorta or femoral artery using any of a variety of well-known techniques. The physician then establishes a second access point in the patient's intercostal region using the port 1078. Using known imaging and guidance techniques, the physician then advances the implantation device 1074 through the patient's aorta or arterial system to the aortic valve annulus 1010. The physician then advances the implantation device 1074 across the aortic valve annulus 1010, through the left ventricle 1050, and out of the heart through the port 1078. At this point, the physician has established a continuous pathway allowing both retrograde (i.e., through the aorta or aortic arch) and antegrade (i.e., through the apex 1060) access to the aortic valve annulus 1010.

According to another exemplary embodiment, the implantation device 1074 includes two portions. The physician introduces a first portion through the aorta or femoral artery to the aortic valve annulus 1010 and introduces a second portion through the apex 1060. According to various embodiments, the physician then couples the two portions together at or near the valve annulus 1010 or the aortic root. In these embodiments, the implantation device 1074 includes any of a variety of known structures for coupling the free ends to one another, so as to form a continuous rail or track. According to other embodiments, the physician employs any of a numerous variety of techniques known in the art to introduce the implantation device 1074. According to various embodiments, the physician employs one or more of the following techniques to implant the device 1074: optionally ballooning the native valve in one variant of the invention, or removing the native valve (e.g., by cutting the valve out of the annulus), optionally using an umbrella capture feature to catch any debris that may result from the cut, and implanting the device 1074.

Once introduced, the implantation device 1074 establishes a pathway between a first opening and second opening in a patient's body. The implantation device is left in place within the heart 102 to provide a tether or "rail" over which other tools or devices may be delivered. Additional tools and devices may be delivered along the rail using either a retrograde (i.e., via the aorta) or an antegrade (i.e., via the apex and left ventricle) approach. The implantation device 1074 allows for one or more than one device to be delivered to the target site at the same time or substantially at the same time. This feature allows flexibility in delivery options and may increase the speed in the successive steps in the valve replacement procedure.

By way of further example, one tool or set of tools can be delivered through the access port from the aorta while a second tool or set of tools can be delivered through the access point in the left ventricle, along a single track spanning both points of access or along separate tracks, one for each access point. An aortic valve (which can be stenotic in many patients) cutter or remover is delivered through the access point in the aorta by a first physician or technician. The native stenotic valve (e.g., aortic valve) is excised, stored in a chamber of the cutter, and then the cutter assembly is removed through the aortic access point. A delivery system for an expandable valve prosthesis can be guided through the ventricular access port and be positioned in the ventricle ready for immediate insertion into position once the cutting operation has been completed. The delivery system can be optionally operated by a second physician or technician and be ready and waiting for deployment. It is appreciated that the speed with which both the cutting and the valve prosthesis deployment operations is greatly increased and the procedure time is greatly reduced using a combination antegrade and retrograde delivery approach. In this way the hemodynamic blood flow for the patient is maintained at an acceptable level while the patient is off-pump or partially off-pump. Similarly, it is appreciated that a variety of tools or modules (or portions thereof) can be guided either antegrade or retrograde along the guidewire.

In various exemplary embodiments of the invention, the cutter or native valve leaflet remover is sized and dimensioned to be delivered through the apex of the heart, while the delivery system including a heart valve prosthesis is sized and dimensioned for delivery through an access point on the aorta. In yet another variant of the invention, an access point can be established at any suitable point in the aortal tree.

By way of further example, a top portion of the cutter can be guided into cutting position along the guidewire along from the aortic access point, while a bottom portion of a cutter can be guided along the guidewire through the access point in the ventricle. The two portions meet at the native valve and perform the cutting and removal operation and then are each removed through the same access areas where they entered the patient.

By way of further example, other modules that can travel along the guidewire can include pumps for assisting in maintaining the patient's hemodynamic flow. The pumps can be positioned in various locations along the guidewire as needed. Other modules (e.g., a cutter or prosthesis delivery module) can then be guided over the pumps to perform their required operations.

As described, the valve access system 1070 allows for delivery of a variety of devices to or near the aortic valve annulus 1010. The system 1070 may be used for example to introduce any of a variety of prosthetic heart valves, including, for example, stented and stentless tissue valves. The system 1070 may also be used to introduce an imaging system to view all or a portion of a procedure. Imaging systems are well-known in the art and include, for example, transesophageal echo, transthoracic echo, intravascular ultrasound imaging (IVUS), and/or a radiopaque dye or contrast fluid. The imaging system may also include an optical viewing device, such as a fiber-optic camera.

The valve access system 1070 allows for delivery of a variety of additional tools or devices, including, for example, the following: leaflet excision tools, leaflet capture devices, imaging devices, prosthetic heart valves, prosthetic valve delivery systems, blood-pump devices, inflation catheters and balloons, debris capture collapsible and expandable umbrellas, stenotic tissue debridement tools, markers located on the guidewire to assist in location of the guidewire at the appropriate location, centering balloons to center the guidewire in the desired orientation, and the like. In yet a further variant, an anti-embolization module is also added. According to various embodiments, the leaflet excision module includes a rigid portion having an actuator exerting sufficient force to cut through a calcified leaflet.

According to another embodiment of the present invention, the valve access system includes one or more interchangeable modules that are configured to be delivered along the implantation device 1074 to the valve annulus 1010. The implantation device 1074 permits one or more modules to be in use at a given time, in series or in parallel. Depending upon the size of the module, an antegrade, retrograde, or combination antegrade and retrograde delivery approach may be chosen. As the apex 1060 is not limited by the size constraints which are presented by percutaneous surgical methods, larger modules or devices may be delivered through the port 1078. Smaller modules may continue to be delivered through the femoral artery approach or directly through a port or incision in the aorta. Ultimately either approach may be chosen at the discretion of one of skill in the art performing the procedure.

In yet another embodiment of the invention, all modules are de-aired, filled with a fluid (e.g., saline), or filled with an appropriate gas (e.g., carbon dioxide or nitrogen) prior to use.

This process eliminates the risk of an embolism occurring through the introduction of any of the modules described below directly into the beating heart of the subject. According to various embodiments, the modules are de-aired using one of the techniques described in co-pending, commonly assigned U.S. patent application Ser. No. 11/851,528, filed on Sep. 7, 2007, entitled "Fluid-Filled Delivery System for in Situ Deployment of Cardiac Valve Prostheses," which is hereby incorporated by reference in its entirety.

Figure 13:
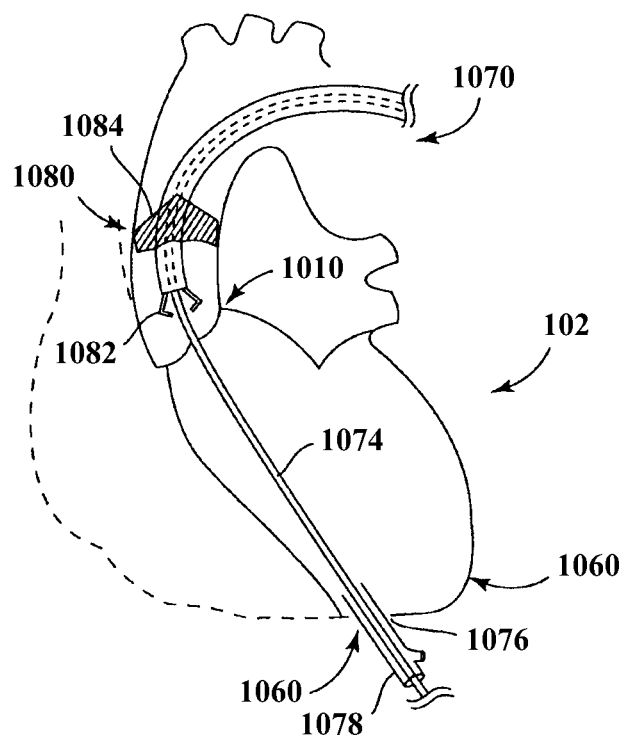
FIG. 13 is a schematic view of the left side of the heart including an implantation device and one interchangeable module according to an embodiment of the present invention.

According to the embodiment of the present invention shown in FIG. 13, the valve access system 1070 includes a leaflet removal (i.e., excision) module 1080, which may include a leaflet cutting tool 1082. The leaflet removal module 1080 includes a rigid portion having an actuator exerting sufficient force to cut through a calcified leaflet. The actuator can be hydraulically or mechanically actuated to provide sufficient force to cut through stenotic native valve tissue. In various embodiments, the actuator is spring actuated. In yet another variant, the actuator is gas actuated. Exemplary leaflet removal or cutting tools are shown and described in U.S. Pat. No. 5,304,189, U.S. Pat. No. 5,370,685, and U.S. Publication 2006/0271081, each of which are incorporated herein by reference.

According to yet a further embodiment of the present invention, as is also shown in FIG. 13, the valve access system 1070 also includes a leaflet capture device 1084. The leaflet capture device 1084 captures the removed portion or portions of the leaflet upon excision and traps any debris from the removal or decalcification of the leaflets. The capture device 1084 entraps and contains the debris or excised portions. The capture device permits removal of the debris from the patient's heart 102.

Figure 14A:
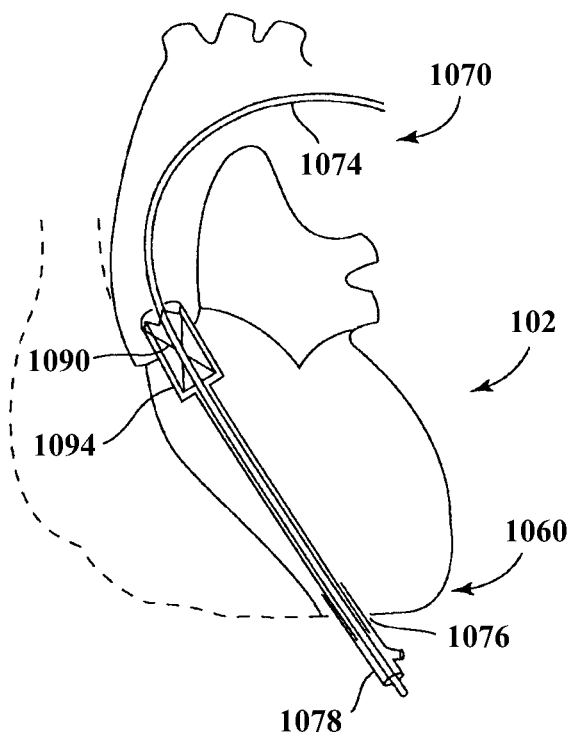
FIGS. 14A and 14B are schematic views of the of the left side of the heart including an implantation device and another interchangeable module according to another embodiment of the present invention.
Figure 14B:
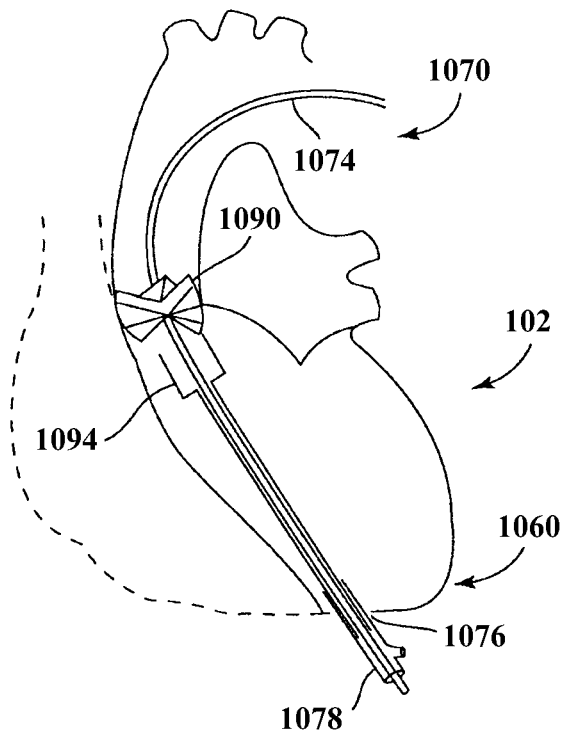

FIGS. 14A and 14B show another embodiment of the valve access system 1070 of the present invention. As shown in FIG. 14A, the system 1070 includes an expandable prosthetic heart valve 1090 retained in a collapsed configuration within a delivery sheath 1094. As described previously, the heart valve 1090 can be crimped onto the delivery system 1070 under water, such that the sheath is fluid filled to prevent embolism. Exemplary expandable prosthetic heart valves are shown and described in U.S. Publication 2006/0178740 and U.S. Publication 2005/0197695, both of which are incorporated herein by reference. An exemplary delivery system for an expandable prosthetic valve is shown and described in commonly-assigned, co-pending U.S. application Ser. No. 11/612,980, entitled "Instrument and Method for In-Situ Deployment of Cardiac Valve Prosthesis", which is incorporated herein by reference. As shown in FIG. 14A, the prosthetic valve 1090 has been delivered over the implantation device 1074 to a target site within or near the aortic valve annulus 1010 via an access port established at or near the apex 1060. As shown, in FIG. 14B, the delivery sheath 1094 can be retracted allowing the expandable prosthetic heart valve 1090 to transition from a collapsed configuration to an expanded configuration, after which the implantation device 1074 can be removed. According to other embodiments, the delivery sheath 1094 could be introduced in a retrograde manner through the aorta or optionally through the aortic arch.

Figure 15:
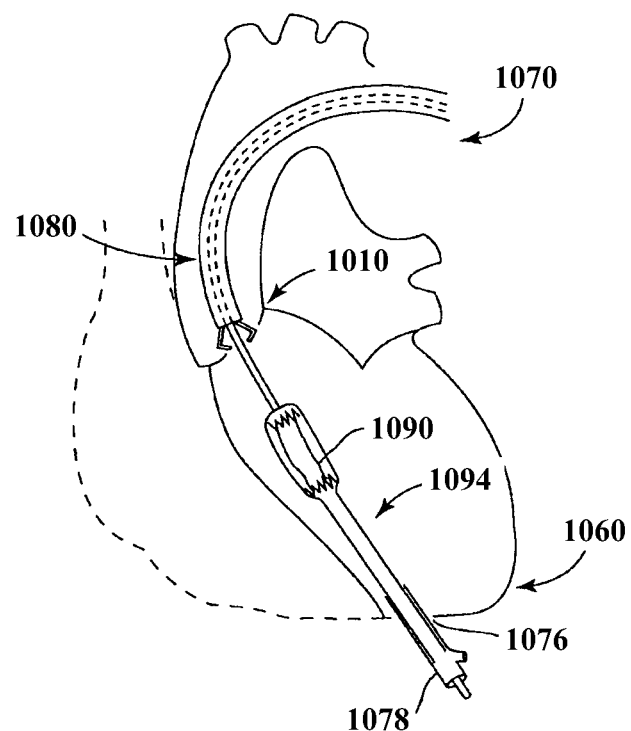
FIG. 15 is a schematic view of the left side of the heart including an implantation device and two interchangeable modules according to yet another embodiment of the present invention.

FIG. 15 shows an embodiment of the valve access system 1070 of the present invention, which includes two interchangeable modules. As shown in FIG. 15, the valve access system 1070 includes an implantation device 1074 and a first module being delivered using an antegrade approach and a second module being delivered using a retrograde approach. According to one embodiment of the present invention, the modules have different functionalities. For example, in various embodiments, the first module is a leaflet cutter 1080 and the second module is an expandable prosthetic valve 1090 contained within a delivery sheath 1094. After the leaflets have been excised from the valve annulus, the expandable prosthetic valve 1090 can be quickly delivered and released to expand within the valve annulus. This configuration can help reduce the time that a patient's heart is beating, without a functioning valve in place, by allowing a physician to deliver both a valve removal device and a valve delivery device at or near the valve annulus 1010, before actually removing the valve leaflets. The configuration is thus helpful for off-pump, beating heart prosthetic valve replacement.

Figure 16:
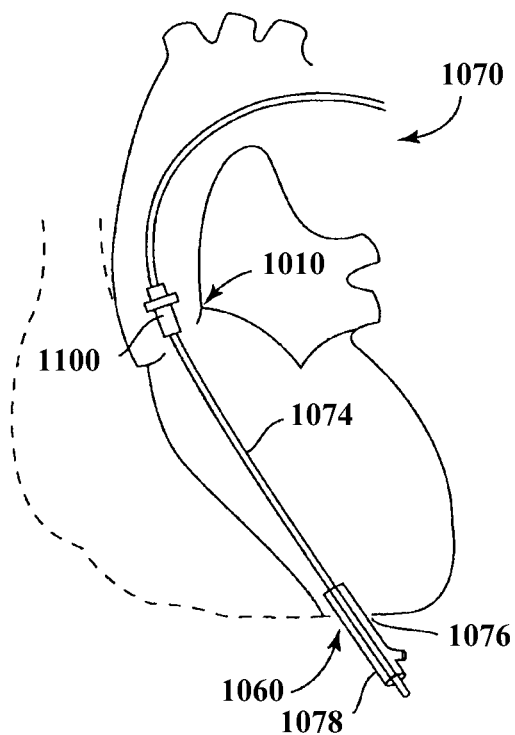
FIG. 16 is a schematic view of the left side of the heart including an implantation device and yet another interchangeable module according to yet another embodiment of the present invention.

According to yet a further embodiment of the present invention, as shown in FIG. 16, the valve access system 1070 includes a blood-pumping device 1100. For example, the blood pumping device is a left ventricular assist device (LVAD) known to those of skill in the art. Exemplary LVADs are shown and described in U.S. Pat. No. 7,144,364, which is incorporated herein by reference. The LVAD can be delivered using either an antegrade or a retrograde approach along the pathway established by the implantation device 1074. The LVAD is then delivered to a target site within the left ventricle or the aorta.

In yet another variant of the invention, two distinct mechanically unconnected tracks are used upon which two mechanically unconnected modules are utilized. In this variant, a first module is configured to be delivered from a first opening in a patient's aortic tree and through the patient's aorta. One or more of the modules described herein may be used. A second module is configured to be delivered through an opening in a ventricle. Again, one or more modules described herein may be used. As with the other embodiments described herein, the fact that two simultaneous or nearly simultaneous access points are used on the patient allows for speed of native valve removal and implantation of a new prosthesis.

Various modifications and additions can be made to the exemplary embodiments discussed without departing from the scope of the present invention. Accordingly, the scope of the present invention is intended to embrace all such alternatives, modifications, and variations as fall within the scope of the claims, together with all equivalents thereof.

We claim:

1. A system for implanting a heart valve prosthesis in a patient's heart, comprising, in combination,
   a heart valve prosthesis having a principal axis extending longitudinally therethrough, the heart valve prosthesis including an armature and prosthetic valve, leaflets, the heart valve prosthesis armature including an annular inflow portion and an annular outflow portion connected by a plurality of axially extending anchoring formations spaced about the principal axis of the heart valve prosthesis and configured to radially protrude beyond the annular inflow portion and annular outflow portion, and
   an apical valve delivery device for delivering the heart valve prosthesis to a target site in the patient's heart, the delivery device comprising:
      a deployment module for expanding the heart valve prosthesis, the deployment module comprising a first deployment element configured to enclose the annular outflow portion and a second deployment element configured to enclose the annular inflow portion, wherein each of the first and second deployment elements are independently operable, and
      markers on the delivery device to assist in location of the delivery device at an appropriate location,
      wherein the first deployment element includes a streamlined cap.

2. The system of claim 1 in which the streamlined cap further comprises a delivery sheath.

3. The system of claim 1 in which the delivery device further comprises a non-embolic gas and or a non-embolic fluid.

4. The system of claim 1 in which the device is bendable.

5. The system of claim 1 further comprising a port for establishing access to an apex of the patient's heart.

6. The system of claim 5 in which the port comprises a valve and or seal configured to provide a blood tight seal during a procedure.

7. The system of claim 1 further comprising an imaging module.

8. A system for implanting a heart valve prosthesis in a patient's heart, comprising, in combination,
 a port for establishing access to an apex of the patient's heart,
 heart valve prosthesis having a principal axis extending longitudinally therethrough, the heart valve prosthesis including an armature and prosthetic valve, leaflets, the heart valve prosthesis armature including an annular inflow portion and an annular outflow portion connected by a plurality of axially extending anchoring formations spaced about the principal axis of the heart valve prosthesis and configured to radially protrude beyond the annular inflow portion and annular outflow portion, and
 an apical valve delivery device for delivering the heart valve prosthesis to a target site in the patient's heart, the delivery device comprising:
 a deployment module for expanding the heart valve prosthesis, the deployment module comprising a first deployment element configured to enclose the annular outflow portion and a second deployment element configured to enclose the annular inflow portion, wherein each of the first and second deployment elements are independently operable, and
 markers on the delivery device to assist in location of the delivery device at an appropriate location,
 wherein the first deployment element includes a streamlined cap.

9. The system of claim 8 in which the streamlined cap further comprises a delivery sheath.

10. The system of claim 8 in which the delivery device further comprises a non-embolic gas and or a non-embolic fluid.

11. The system of claim 8 in which the device is bendable.

12. The system of claim 8 in which the port comprises a valve and or seal configured to provide a blood tight seal during a procedure.

13. The system of claim 8 further comprising an imaging module.

* * * * *